US006348625B1

United States Patent
Anderson

(10) Patent No.: US 6,348,625 B1
(45) Date of Patent: Feb. 19, 2002

(54) METHOD FOR PREPARING SOME 1-ADAMANTANCECARBOXAMIDES

(76) Inventor: Gloria Long Anderson, 560 Lynn Valley Rd. SW., Atlanta, GA (US) 30311-2331

( * ) Notice: Subject to any disclaimer, the term of this patent is extended or adjusted under 35 U.S.C. 154(b) by 0 days.

(21) Appl. No.: 09/709,076

(22) Filed: Nov. 10, 2000

(51) Int. Cl.$^7$ .............................................. C07C 231/02
(52) U.S. Cl. ....................................... 564/133; 564/188
(58) Field of Search ................................. 564/133, 188

(56) References Cited

U.S. PATENT DOCUMENTS 5,382,673 A * 1/1995 Clark et al. .................. 548/239

FOREIGN PATENT DOCUMENTS

WO          9732835       *    9/1997

OTHER PUBLICATIONS

Novakov et al, Khim. Farm. Zhu, No. 4, pp 454–458, 1985.*
Danilenko et al, Khim. Farm. Zhu., No. 5, pp 49–52, 1974.*
Aigami et al, J. Med. Chem., vol. 18, No. 7, pp 712–721, 1975.*
Krasutski i et al, Khim. Farm. Zhu., vol. 19, No. 7, pp 825–829, 1985.*
Fridman et al, Khim. Farm. Zhu, vol. 8, No. 7, pp 396–398., 1974.*
Danilenko et al, Khim. Farm. Zhu, vol. 10. No. 6, pp 37–41, 1976.*
Stetter et al, Chem. Ber., vol. 93, pp 226–230, 1960.*
Anderson et al, Synth. Commun., vol. 18, pp 1967–1974, 1988.*
Anderson et al, The Chemist, pp 7–10, Jan./Feb. 2000.*
Yarovenko et al, J. Gen. Chem. USSR., vol. 29, pp 2125–2128, 1959.*

* cited by examiner

*Primary Examiner*—Shailendra Kumar

(57) ABSTRACT

This invention relates to a method for the novel preparation of 1-adamantanecarboxamides and 1-adamantaneacetamides. Adamantanecarboxamides and adamantaneacetamides are prepared in high yields (80–100%) by treating adamantanecarboxylic acid and adamantaneacetic acid with N,N-diethyl-1,1,2,3,3,3-hexafluoropropylamine, followed by addition of aqueous ammonia or the appropriate amine. The procedure, carried out at ambient temperature using common laboratory equipment, is both convenient and rapid, requiring no more than one or two hours. Several reactions can be carried out simultaneously.

22 Claims, No Drawings

METHOD FOR PREPARING SOME 1-ADAMANTANCECARBOXAMIDES

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION

This invention relates to a method for the novel preparation of some N-substituted-1-adamantanecarboxamides and some 1-adamantaneacetamides by treating 1-adamantanecarboxylic acid or 1-adamantaneacetic acid with N,N-diethyl-1,1,2,3,3,3-hexafluoropropylamine, followed by the addition of aqueous ammonia or amines.

The amide linkage is present in peptides and proteins. Moreover, the amide functional group is present in many medicinal compounds. Thus, reactions that lead to the formation of the amide linkage and/or the amide functional group are useful in pharmaceutical research as well as the development of drugs.

N-Substituted-1-adamantanecarboxamides are useful as potential antiviral agents as well as intermediates in the synthesis of antiviral agents. Therefore, this invention has potential commercial application as a convenient and rapid method for the preparation of adamantanecarboxamides, other carboxamides, more complex compounds containing the amide functional group, and compounds containing the amide linkage.

Traditionally, carboxamides in general, and adamantanecarboxamides in particular (Novakov, et al., *Khim-Farm. Zh.*, 1987, 21(4), 454–8; Danilenko, et. al., *Khim.-Farm. Zh.*, 1976, 10(5), 49–52) have been prepared from the corresponding acids via the acid chlorides. In general, this method is long and tedious.

According to most methods, preparation of acid chlorides requires refluxing the acids in excess thionyl chloride from thirty minutes to as long as several hours, followed by distillation to remove unreacted thionyl chloride. According to one method 1,3-adamantane(bis)acetic acid was refluxed in excess thionyl chloride for twenty-four hours to prepare the corresponding acid chloride (Aigami, et. al., *J. Med. Chem.*, 1975, 18(7), 713–21). Another method for the preparation of some adamantanecarboxamides involved refluxing the corresponding acid in thionyl chloride and benzene for eight hours, followed by distillation to remove the benzene and excess thionyl chloride (Krasutskii, et al., *Khim.-Farm. Zh.*, 1985, 19(7), 825–29). Still another method involved refluxing the adamantanecarboxylic acids in thionyl chloride containing a catalytic amount of N,N-dimethylformide (Fridman, et. al., *Khim.-Farm. Zh.*, 1974, 8(7), 6–8). Also, adamantanecarboxamides have been prepared by heating the corresponding acids with phosphorus pentachloride in carbon tetrachloride for one hour (Danilenko, et. al., *Khim.-Farm. Zh.*, 1976, 10(6), 37–41). Usually, after the acid chloride has been isolated from excess co-reactant, solvent, and/or by products, it is dissolved in a solvent such as anhydrous tetrahydrofuran or anhydrous dioxane, aqueous ammonia or the amine is added, and the mixture is allowed to stand for about twelve hours.

There are several disadvantages to using the methods described above. These methods require: 1) reflux and distillation apparatus; 2) traps for the hydrogen chloride and sulfur dioxide evolved in the thionyl chloride reaction; 3) heating apparatus; and 4) isolation of the acid chloride. Thus, unlike the method described in this invention, the above methods are long and tedious.

Additionally, adamantanecarboxamides have been prepared in our laboratories using DATE [1-(N,N-diethylamino)-1,1,2-trifluoro-2-chloroethane] (Anderson, et. al., *Synthetic Comm.*, 1988, 18(16 & 17), 1967–1974; Anderson, et. al., *The Chemist*, January/February 2000, 7–10). The reagent DATE was prepared from diethylamine and chlorotrifluoroethylene, according to a modified procedure of Yarovenko and Raksha (Yarovenko and Raksha, *J. Gen. Chem. USSR*, 1959,29,2125–28). Chlorotrifluoroethylene gas was bubbled slowly into diethylamine contained in a gas drying tube cooled by an ice water bath. This was continued for at least twelve hours, and the product was collected by vacuum distillation. There are several disadvantages to using this reagent. First, the procedure for preparation of the reagent required about twenty four hours. Second, the reagent is not very stable at room temperature and decomposes within a few days even when stored in the refrigerator. Third, preparation of the reagent requires somewhat sophisticated equipment. The reagent used in this invention is commercially available from Lancaster Synthesis in Windham, N.H. Further, the reagent is stable over a long period of time. Thus, unlike the method described in this invention, the procedure using DATE is long and tedious.

BRIEF SUMMARY OF THE INVENTION

The invention described herein provides a method for preparing adamantanecarboxamides and adamantaneacetamides in high yields (80–100%) by treating the 1-adamantanecarboxylic acid or 1-adamantaneacetic acid with N,N-diethyl-1,1,2,3,3,3-hexafluoropropylamine, followed by addition of aqueous ammonia or the appropriate amine. The procedure is convenient and rapid, requiring no more than one or two hours. Several reactions can be carried out simultaneously.

DETAILED DESCRIPTION OF THE INVENTION

The carboxamides are prepared by a procedure that is carried out in a wide mouth polyethylene bottle on a magnetic stirrer at ambient temperature. Isolation of the amide is completed by filtering and washing with water, followed by a small amount of ethyl ether. The entire reaction, including isolation of the product, can be completed within one or two hours. The method works equally as well for the preparation of 3-substituted-1-adamantanecarboxamides and 3-substituted-1-adamantaneacetamides. In the case of 3-hydroxy-1-adamantanecarboxylic acid and 3-hydroxy-1-adamantaneacetic acid, the hydroxy group must be protected otherwise it is converted to a fluoro group. Thus, 3-hydroxy-1-adamantanecarboxylic acid yields 3-fluoro-1-adamantanecarboxamide.

The procedure consists of adding the 1-adamantanecarboxylic acid to N,N-diethyl-1,1,2,3,3,3-hexafluoropropylamine contained in a wide mouth polyethylene bottle during which time the acid fluoride forms immediately through an exothermic reaction. The rate of addition of the acid may be adjusted to control the temperature and prevent the evolution of hydrogen fluoride or the reaction bottle may be cooled in an ice water bath briefly.

The intermediate acid fluoride is not isolated. After the reaction mixture cools to room temperature by allowing it to stand at room temperature or by cooling it in an ice water bath, cold aqueous ammonia or the desired amine is added and the amide precipitates immediately. An excess of an inexpensive amine is added to convert the hydrogen fluoride to the amine salt. For more expensive amines, aqueous base is added to convert the hydrogen fluoride to the salt prior to the addition of the amine. The amide is collected by filtration and washed copiously with water followed by a minimum amount of ethyl ether. For large scale preparations the oily amide by product, N,N-diethyl-2,3,3,3-tetrafluoropropionamide, can be collected from the filtrate by separation from the water phase using a separatory funnel. Similarly, for large scale preparations, the hydrogen fluoride salt of ammonia or the amine can be recovered by evaporation of the water. Several reactions can be carried out simultaneously.

Some examples of the preparation of compounds, presented as illustrations and not intended to be limiting, are as follows.

EXAMPLE 1

Preparation of 1-Adamantanecarboxamide

1-Adamantanecarboxylic acid (10.8 g, 0.06 mole) was added to N,N-diethyl-1,1,2,3,3,3-hexafluoropropylamine (13.4 g, 0.06 mole) contained in a wide mouth polyethylene bottle with magnetic stirring. The acid dissolved immediately during which time a highly exothermic reaction occurred. The reaction mixture was allowed to cool to room temperature and cold aqueous ammonia (250 ml) was added slowly. A heavy precipitate of the amide appeared almost immediately. After the addition was complete, the reaction mixture was stirred for about fifteen minutes. The 1-adamantanecarboxamide was collected and washed copiously with water followed by ethyl ether and dried. Yield: 10.7 g, 100%; mp 189.4–190.2° C. (Lit. mp 189° C., Stetter, et. al., *Chem. Ber.*, 1960, 226–230). The analytical sample was recrystallized from cyclohexane and sublimed. Anal. Calcd. for $C_{11}H_{17}NO$: C, 73.76; H, 9.49; N, 7.82. Found: C, 73.67; H. 9.60; N, 7.78.

EXAMPLE 2

Preparation of 1-Adamantaneacetamide

1-Adamantaneacetic acid (11.7 g, 0.06 mole) was dissolved in N,N-diethyl-1,1,2,3,3,3-hexafluoropropylamine (13.4 g, 0.06 mole) during which time a highly exothermic reaction occurred. The reaction mixture was allowed to cool to room temperature and cold aqueous ammonia (250 ml) was added slowly. The 1-adamantaneacetamide was isolated as described in example 1 to yield 10.5 g, 90.6 %; mp 173.6–174.0° C. The analytical sample was recrystallized from cyclohexane and sublimed. Anal. Calcd. for $C_{12}H_{19}NO$: C, 74.63; H, 9.89; N, 7.25. Found: C, 74.36; H, 9.84; N, 7.15.

EXAMPLE 3

Preparation of N-Cyclohexyl-1-Adamantanecarboxamide

1-Adamantanecarboxylic acid (10.8 g, 0.06 mole) was dissolved in N,N-diethyl-1,1,2,3,3,3-hexafluoropropylamine (13.4 g, 0.06 mole) as described in example 1. After the reaction mixture cooled to room temperature, cyclohexylamine (14.88 g, 17.2 ml, 0.15 mole) was added slowly and a heavy precipitate of the amide appeared almost immediately. The N-cyclohexyl-1-adamantanecarboxamide was isolated as described in example 1 to give 14.8 g, 94.4%; mp 199.3–200.4° C. The analytical sample was recrystallized from cyclohexane and sublimed. Anal. Calcd. for $C_{17}H_{27}NO$: C, 78.18; H. 10.34; N, 5.36. Found: C, 77.97; H, 10.46; N, 5.32.

EXAMPLE 4

Preparation of N-p-Methoxyphenyl-1-Adamantanecarboxamide

1-Adamantanecarboxylic acid (10.8 g, 0.06 mole) was dissolved in N,N-diethyl-1,1,2,3,3,3-hexafluoropropylamine (13.4 g, 0.06 mole) as described in example 1. After the reaction mixture cooled to room temperature, a solution of p-anisidine (18.5 g, 0. 15 mole) in ethyl ether (minimum amount) was added and the reaction mixture was stirred for about an hour. The ethyl ether was removed at the rotary evaporator and the N-p-methoxyphenyl-1-adamantanecarboxamide was isolated as described in example 1 to give 15.8 g, 92%; mp 186–187° C. The analytical sample was recrystallized from cyclohexane and sublimed. Anal. Calcd. for $C_{18}H_{23}NO_2$: C, 75.80; H, 8.07; N, 4.91. Found: C, 75.69; H, 8.17; N, 4.92.

Further examples of some of the compounds prepared according to these procedures are given in Table 1. The N-substituted-1-adamantanecarboxamides shown in Table 1 are: Example 5, N-isopropyl-1-adamantanecarboxamide; Example 6, N-tert-butyl-1-adamantanecarboxamide; Example 7, N-sec-butyl-1-adamantanecarboxamide; Example 8, N-α-methylbenzyl-1-adamantanecarboxamide; Example 9, N-p-methylphenyl-1-adamantanecarboxamide; Example 10, N-2-(1-methoxypropyl)-1-adamantanecarboxamide; Example 11, N-3,4-dinethoxyphenyl-1-adamantanecarboxamide; Example 12, N-phenyl-1-adamantanecarboxamide; Example 13, N-p-n-butylphenyl-1-adamantanecarboxamide; Example 14, N-m-bromophenyl-1-adamantanecarboxamide; Example 15, N-methyl-1-adamantanecarboxamide; and Example 16, N-ethyl-1-adamantanecarboxamide.

TABLE 1

Some N-Substituted-1-Adamantanecarboxamides Prepared According To This Method

| Example Number | N-Substituent | % Yield | MP ° C. | Anal Calcd For | Calculated | | | Found | | |
|---|---|---|---|---|---|---|---|---|---|---|
| | | | | | C | H | N | C | H | N |
| 5 | (CH₃)₂CH— | 89.3 | 179.6–180.0 | $C_{14}H_{23}NO$ | 76.03 | 10.40 | 06.33 | 76.08 | 10.50 | 06.37 |
| 6 | (CH₃)₃C— | 84.5 | 182.7–184.0 | $C_{15}H_{25}NO$ | 76.61 | 10.63 | 05.95 | 76.65 | 10.75 | 05.99 |
| 7 | CH₃—CH₂—CH(CH₃)— | 93.5 | 166.0–167.0 | $C_{15}H_{25}NO$ | 76.61 | 10.63 | 05.95 | 76.35 | 10.76 | 05.89 |
| 8 | C₆H₄—CH(CH₃)— | 95.1 | 170.6–170.7 | $C_{19}H_{25}NO$ | 80.58 | 08.83 | 04.94 | 80.75 | 08.90 | 04.94 |
| 9 | P—CH₃—C₆H₄— | 94.6 | 192.1–192.5 | $C_{18}H_{23}NO$ | 80.31 | 08.54 | 05.20 | 80.28 | 08.66 | 05.14 |
| 10 | CH₃O—CH₂—CH(CH₃)— | 91.1 | 114.2–114.6 | $C_{15}H_{25}NO_2$ | 71.73 | 09.95 | 05.57 | 71.77 | 09.98 | 05.61 |

TABLE 1-continued

Some N-Substituted-1-Adamantanecarboxamides Prepared According To This Method

| Example Number | N-Substituent | % Yield | MP °C. | Anal Calcd For | Calculated C | H | N | Found C | H | N |
|---|---|---|---|---|---|---|---|---|---|---|
| 11 | 3,4-$(CH_3O-)_2$—$C_6H_3$— | 95.1 | 226.1–227.6 | $C_{19}H_{23}NO_3$ | 72.40 | 07.93 | 04.44 | 72.45 | 07.99 | 04.41 |
| 12 | $C_6H_5$— | 91.4 | 200.2–202.3 | $C_{17}H_{21}NO$ | 80.01 | 08.23 | 05.49 | 80.04 | 08.29 | 05.55 |
| 13 | p-$CH_3$—$(CH_2-)_3$—$C_6H_4$— | 87.8 | 134.5–134.9 | $C_{21}H_{29}NO$ | 81.04 | 09.32 | 04.50 | 81.07 | 09.42 | 04.53 |
| 14 | m-Br—$C_6H_4$— | 96.3 | 191.0–191.5 | $C_{17}H_{20}NOBr$ | 61.12 | 05.99 | 04.19 | 61.24 | 06.06 | 04.17 |
| 15 | $CH_3$— | 81.6 | 144.4–145.1 | $C_{12}H_{19}NO$ | 74.63 | 09.84 | 07.25 | 74.68 | 09.93 | 07.28 |
| 16 | $CH_3$—$CH_2$— | 81.3 | 128.1–128.5 | $C_{13}H_{21}NO$ | 75.38 | 10.14 | 06.76 | 75.34 | 10.16 | 06.82 |

REFERENCE CITED

1. Novakov, I. A., Kulev, I. A., Radchenko, S. S., Birznieks, K. A., Boreko, E. I., Vladyko, G. V., and Korobehenko, L. V., "Synthesis and Antiviral Activity of the Hydrochlorides of AlicyclicMono- and Diamines," Khim.-Farm. Zh., 1987,21(4), 454–8. (English Translation)
2. Danilenko, G. I., Votyakov, V. I., Andreeva, O. T., Timofeeva, M. M., Shashikhina, M. N., Denisova, L. V., Boreko, E. I., Bruskova, I. V., Dikolenko, E. I., and Smirnova, N. A., "Synthesis and Biological Activity of Adamantane Derivatives.III. Virus Inhibiting Effect of 1-(4-Aminophenyl)adamantane Derivatives," Khim.-Farm. Zh., 1976,10(5), 49–52. (English Translation)
3. Aigami, K, Inamoto, Y., Takaishi N., and Hattori, K, "Biologically Active Polycycloalkanes. 1. Antiviral Adamantane Derivatives," J. Med. Chem., 1975, 18(7), 713–21.
4. Krasutskii, P. A., Semenova, I. G., Novikova, M. I., Yurchenko, A. G., Leont'eva, N. A., and Veselovskaya, T. V., "Amino Acids of the Adamantane Series I. Synthesis and Antiviral Activity of Alpha Amino Acids of the Adamantane Series and their Derivatives," Khim.-Farm. Zh., 1985, 19(7), 825–29. (English Translation)
5. Fridman, A. L., Zalesov, V. S., Moiseev, I. K, Kolobov, N. A., and Dobrilkin, K. V., "Synthesis and Physiological Activity of Some Adamantanecarboxylic Acids and Their Derivatives," Khim. -Farm. Zh., 1974, 8(7), 6–8. (English Translation)
6. Danilenko, G. I., Votyakov, V. I., Andreeva, O. T., Boreko, E. I., Denisova, L. V., Shashikhina, M. N., Timofeeva, M. N., Dilolenlo, E. I., and Utocbka, T. N., "Synthesis and Biological Activity of Adamantane Derivatives. IV. Virus Inhibiting Effect of Some Adamantylamines," Khim. -Farm. Zh., 1976, 10(6), 37–41. (English Translation)
7. Stetter, H., Mayer, J., Schwarz, M., and Wulaf, K., "Uber Verbindmigen mit Urotropin-Struktur. XVI. Beitrage zur Chemie der Adamantyl-(1)-Derivative," Chem. Ber., 1960,93, 226–30. (German)
8. Anderson, G. L., Burks, W. A., and Harruna, I. I., "Novel Synthesis of 3-Fluoro-1-Amino-Adamantane And Some Of Its Derivatives," Synthetic Communications 1988, 18(16 & 17), 1967–1974
9. Anderson, G. L. and Kaimari, T., "Novel Synthesis Of Some 3-Halo-1-Aminoadamantanes," The Chemist, January/February 2000, 7–10
10. Yarovenko, N. N. and Raksha, M. A., "Fluorination By Means of Alpha Fluorinated Amines," J. Gen. Chem USSR, 1959, 29, 2125–28 (English Translation)

What I claim as my invention is a procedure comprising:
1. A method for preparing organic compounds containing the amide linkage conveniently and rapidly by treating the corresponding carboxylic acid functional group with N,N-diethyl-1,1,2,3,3,3-hexafluoropropylamine followed by ammonia.
2. A method for preparing organic compounds containing the amide functional group conveniently and rapidly by treating the corresponding carboxylic acid functional group with N,N-diethyl-1,1,2,3,3,3-hexafluoropropylamine followed by ammonia.
3. A method for preparing organic carboxamides conveniently and rapidly by treating the corresponding carboxylic acids with N,N-diethyl-1,1,2,3,3,3-hexafluoropropylamine followed by aqueous ammonia or the appropriate amines.
4. A method for preparing adamantanecarboxamides conveniently and rapidly by treating adamantanecarboxylic acid with N,N-diethyl-1,1,2,3,3,3-hexafluoropropylamine followed by aqueous ammonia or the appropriate amines.
5. The method of claim 3 wherein the product is 1-adamantaneacetamide.
6. The method of claim 4 wherein the product is 1-adamantanecarboxamide.
7. The method of claim 4 wherein the product is N-cyclohexyl-1-adamantanecarboxamide.
8. The method of claim 4 wherein the product is N-p-methoxyphenyl-1-adamantanecarboxamide.
9. The method of claim 4 wherein the product is N-isopropyl-1-adamantanecarboxamide.
10. The method of claim 4 wherein the product is N-tert-butyl-1-adamantaneboxamide.
11. The method of claim 4 wherein the product is N-sec-butyl-1-adamantanecarboxamide.
12. The method of claim 4 wherein the product is N-α-methylbenzyl-1-adamantanecarboxamide.
13. The method of claim 4 wherein the product is N-p-methylphenyl-1-adamantanecarboxamide.
14. The method of claim 4 wherein the product is N-2-(1-methoxypropyl)-1-adamantanecarboxamide.
15. The method of claim 4 wherein the product is N-3,4-dimethoxyphenyl-1-adamantanecarboxamide.
16. The method of claim 4 wherein the product is N-phenyl-1-adamantanecarboxamide.
17. The method of claim 4 wherein the product is N-p-n-butylphenyl-1-adamantanecarboxamide.
18. The method of claim 4 wherein the product is N-m-bromophenyl-1-adamantanecarboxamide.
19. The method of claim 4 wherein the product is N-methyl-1-adamantanecarboxamide.
20. The method of claim 4 wherein the product is N-ethyl-1-adamantanecarboxamide.
21. The method of claim 4 wherein the side products, ammonium fluoride and amine hydrofluorides, can be recovered.
22. The method of claim 4 wherein the side product, N,N-diethyl-2,3,3,3-tetrafluoropropionamide can be recovered.

* * * * *